Dec. 23, 1969 H. DIEDE Plant Pat. 2,956
APPLE TREE
Filed March 25, 1968
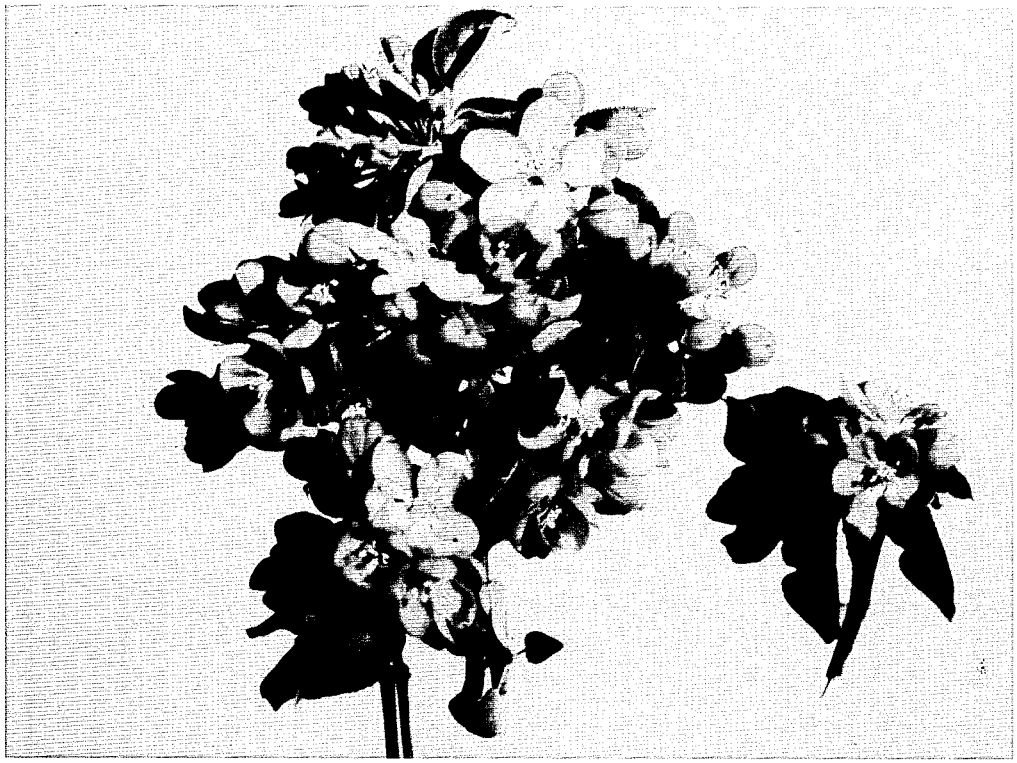
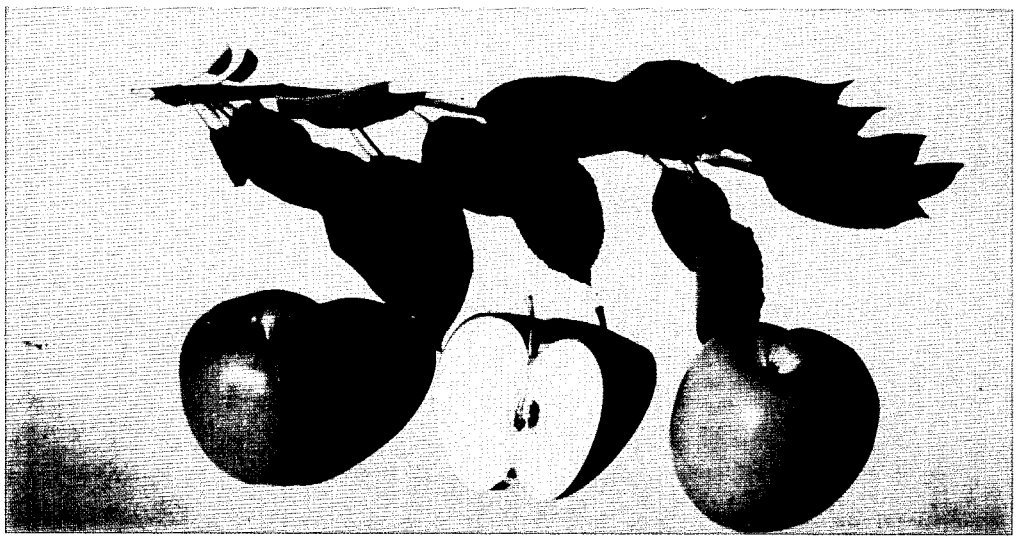
Inventor.
Herbert Diede
By: Robb & Robb
Attorneys.

United States Patent Office

Plant Pat. 2,956
Patented Dec. 23, 1969

2,956
APPLE TREE

Herbert Diede, Wenatchee, Wash., assignor to Stark Bro's Nurseries & Orchards Company, Louisiana, Mo., a corporation of Missouri Filed Mar. 25, 1968, Ser. No. 715,941
Int. Cl. A01h 5/08
U.S. Cl. Plt.—35 1 Claim The present invention relates to a new and distinct variety of apple tree which was discovered by me as a bud mutation or sport of the apple variety commonly known as the Mood Apple (unpatented) which is extensively distributed and sold in commerce by the assignee hereof under the registered trademark "Starking Delicious," said discovery having been made by me in my cultivated orchard situated in Chelan County, Washington.

At the time of my discovery, I was growing in my orchard aforesaid a block of trees of the Mood Apple variety, and in the course of one of my inspections of this orchard to determine the stage of development of the blooms, my attention was attracted to one limb on a particular tree which bore some blooms which were distinctly different from all other blooms in the same block of Mood Apple trees. Closer inspection and prolonged observation of this particular tree convinced me that the distinctive blooms thereon were the result of a bud mutation or sport, and I thereupon took prompt steps to preserve this tree and to keep it under close observation. I found that the fruit produced by the mutation generally resembled that of the Mood Apple variety, but developed a more intense and attractive color. In due course, I asexually reproduced the new mutation, as performed on my behalf by grafting scions on a tree growing in the Tree Fruit Experiment Station at Wenatchee, Wash., as well as on trees being grown by my assignee at Louisiana, Mo. Continued observations and tests of the original mutation on the mother tree and the progeny resulting therefrom by grafting, as aforesaid, over a prolonged period of years, have conclusively demonstrated that the mutation is definitely a new and distinct variety, as particularly evidenced by the following unique combination of characteristics which are outstanding therein and which distinguish it from the standard Mood Apple variety, as well as from all other apple varieties of which I am aware:

(1) A general resemblance of the tree and fruit to the Mood Apple variety (unpatented) which is distributed in commerce under the registered trademark "Starking Delicious";

(2) Purplish-Pink blooms which are much darker and quite distinctive in comparison with the blooms of the Mood Apple variety; and (3) A more intense, bright and attractive solid red color of the fruit.

The accompanying drawing shows typical specimens of the foliage as borne on a typical branch section, as well as typical specimens of the fruit, and with one of the fruit specimens being shown in cross section, all as depicted in color as nearly true as it is reasonably possible to make the same in a color illustration of this character.

The following is a detailed description of my new variety, with color terminology in accordance with Ridgway's Color Standards and Nomenclature (hereinafter abbreviated as (R)), Munsell Color Chart (hereinafter abbreviated as (M)), and the Horticultural Colour Guide (hereinafter abbreviated as (HCG)), as indicated, except where general color terms of ordinary dictionary significance are obvious:

Locality where grown and observed: Louisiana, Mo.

Dates of first and last pickings: About September 10 and September 20, respectively.

Tree: Medium large size; vigorous; spreading; medium tall; vase-formed; rapid growing; hardy; medium productive; regular bearing.

*Branches.*—Medium thickness; smooth; little-branching. Color—Moderate Reddish-Brown, Hue 7.5R 3/6 (M). Lenticels—medium few in number; medium small size.

*Leaves.*—Medium large size; medium width; medium length; ovate; taper-pointed; thick; rugose. Length—about 3½ inches. Width—about 2⅛ inches. Color—Ivy Green, Plate 0960, page 187, vol. 2 (HCG) when mature, but reddish when young at time of blossoming. Margin—coarsely serrate. Petiole—medium length (about 1 inch long); thick.

Flowers: Large size.

*Dates of first and full bloom.*—About April 22 and April 28, respectively; medium early as compared with other varieties.

*Color.*—Light Purplish-Pink, Hue 2.5RP 8/5 (M), streaked with Moderate Purplish-Pink, Hue 2.5RP 7/8 (M).

Fruit:

*Maturity when described.*—Hard ripe (about September 14).

*Size.*—Uniform. Axial diameter—about 2⅞ inches. Transverse diameter—about 3 inches.

*Form.*—Conical; slightly ribbed.

*Cavity.*—Symmetrical; acute; undulate. Markings—russet.

*Basin.*—Depth—about 9/16 inch. Breadth—about 1⅛ inches. Markings—Buff Citrine, Plate XVI, Color No. 19′, Tone *k* (R).

*Stem.*—Slender; pubescent. Length—about 1¼ inches. Breadth—about 1/16 inch.

*Calyx.*—Closed; segments persistent; narrowly lanceolate; acuminate; about ¼ inch long; approximate at base; converged from base toward center; both outer and inner surfaces pubescent.

*Skin.*—Thick; tough; smooth; glossy; waxed. Dots—conspicuous; many; large; even; ruptured; circular; color—Pale Ochraceous Buff, Plate XV, Color No. 15′ (R); distribution—distributed over entire surface, but more numerous toward calyx end. Color markings—striped; self-colored; color—Strong Red, Hue 5R 4/12 (M), with stripes of Deep Purplish-Red, Hue 10RP 3/10 (M).

*Scarfskin.*—Wanting.

*General color effect.*—Bright solid red.

*Flesh.*—Rather juicy. Color—satiny white, with greenish tint. Texture—firm; fine. Flavor—mild. Aroma—distinct. Quality—good.

*Core.*—Median. Bundle area—medium large; oblate; unsymmetrical at base; acute at base. Halves of core—unequal. Bundles—inconspicuous, in one whorl; color—green. Core lines—meeting. Carpellary area—indistinct; large. Calyx tube—pubescent toward base, apex broadly obconic; entire depth—about ⅜ inch. Styles—present; distinct toward base. Stamens—in one distinct whorl; median. Seed cells—axile; cell walls—thin, tough; length—about 9/16 inch, breadth—about ¼ inch; longitudinal section—obovate, obtuse at apex; surface—fissured, tufted; cross section—narrow.

Seeds:

*Average number.*—6 perfect and 1 imperfect, usually with 2 seeds per cell. Length—about 11/32 inch. Breadth—about 3/16 inch.

*Form.*—Acute.

*Color.*—Moderate Reddish-Brown, Hue 10R 4/9 (M).

I claim:

1. A new end distinct variety of apple tree, substantially as herein shown and described, characterized particularly as to novelty by the unique combination of a general resemblance of the tree and fruit to the Mood Apple variety (unpatented) which is distributed in commerce under the registered trademark "Starking Delicious," Purplish-Pink blooms which are much darker and quite distinctive in comparison with the blooms of the Mood Apple variety, and a more intense, bright and attractive solid red color of the fruit.

No references cited.

ROBERT E. BAGWILL, Primary Examiner